United States Patent
Brivet et al.

(10) Patent No.: US 6,372,942 B1
(45) Date of Patent: Apr. 16, 2002

(54) PENTENOIC ACID HYDROXYCARBONYLATION METHOD

(75) Inventors: Jacques Brivet, Bron; Eric B. Henriet; Carl Patois, both of Lyons; Robert Perron, Charly, all of (FR)

(73) Assignee: Rhodia Fiber & Resin Intermediates, Courbevoie Cedex (FR)

(*) Notice: Subject to any disclaimer, the term of this patent is extended or adjusted under 35 U.S.C. 154(b) by 0 days.

(21) Appl. No.: 09/194,969

(22) PCT Filed: May 29, 1997

(86) PCT No.: PCT/FR97/00940

§ 371 Date: Mar. 17, 1999

§ 102(e) Date: Mar. 17, 1999

(87) PCT Pub. No.: WO97/47580

PCT Pub. Date: Dec. 18, 1997

(30) Foreign Application Priority Data

Jun. 7, 1996 (FR) .............................. 96 07380

(51) Int. Cl.⁷ .............................. C07C 55/00
(52) U.S. Cl. ........................ 562/590; 562/591
(58) Field of Search .................... 562/590, 591

(56) References Cited

U.S. PATENT DOCUMENTS 4,622,423 A * 11/1986 Burke
4,788,333 A * 11/1988 Burke
5,292,944 A * 3/1994 Atadan et al.

FOREIGN PATENT DOCUMENTS

FR       WO 94/21586      * 9/1994

* cited by examiner

Primary Examiner—Gary Geist
Assistant Examiner—Robert W. Deemie
(74) Attorney, Agent, or Firm—Burns, Doane, Swecker & Mathis, L.L.P.

(57) ABSTRACT

The invention discloses pentenoic acid hydroxycarbonylation into adipic acid. More particularly, it concerns one pentenoic acid hydroxycarbonylation method involving reaction water and carbon monoxide, in the presence of a catalyst comprising at least rhodium and/or iridium and an iodinated or brominated catalytic promoter. In the method, the catalyst is derived at least in part from a previous pentenoic acid hydroxycarbonylation operation. The reaction is effected in the presence of an amount of branched carboxylic diacids having 6 carbon atoms not exceeding 200 grams per kilogram reaction mixture.

16 Claims, No Drawings

PENTENOIC ACID HYDROXYCARBONYLATION METHOD

The present invention relates to the hydroxycarbonylation of pentenoic acids to adipic acid.

During the hydroxycarbonylation of pentenoic acids, principally 3-pentenoic acid, in the presence of a catalyst and a promoter, to give adipic acid, there are minor but nevertheless significant amounts of branched carboxylic diacids which are isomers of adipic acid, essentially 2-methylglutaric acid and 2-ethylsuccinic acid, as well as traces of 2,2-dimethylsuccinic acid.

Following separation of the adipic acid, the unconverted pentenoic acid, the catalyst, the promoter and various byproducts, such as gamma-valerolactone, are recycled into the hydroxycarbonylation reactor.

However, although it is advantageous in terms of the economics of the process to recycle to best effect the unconverted pentenoic acid, the catalyst, the promoter and the byproducts which are capable of being converted, at least partially, to adipic acid, the applicant has found that the recycling of excessively large amounts of branched carboxylic diacids has an adverse effect on the activity of the catalyst in the hydroxycarbonylation reaction of pentenoic acid.

Besides this effect of deactivating the catalyst, the presence of branched diacids is clearly harmful to the purity of the adipic acid, in particular by its trapping of the metal catalyst during the crystallization of the said adipic acid.

The present invention therefore relates more particularly to a process for hydroxycarbonylating pentenoic acid by reaction with water and carbon monoxide in the presence of a catalyst comprising at least rhodium and/or iridium and of an iodine- or bromine-containing promoter, in which process the catalyst originates at least in part from a prior operation of hydroxycarbonylation of pentenoic acid, characterized in that the reaction is carried out in the presence of an amount of branched carboxylic diacids having 6 carbon atoms of less than or equal to 200 grams per kilogram of reaction mixture.

The terms branched carboxylic diacids and branched diacids are equivalent in the present text and also embrace the anhydride forms corresponding to these diacids.

In the process according to the invention the hydroxycarbonylation reaction is preferably conducted in the presence of an amount of branched carboxylic diacids having 6 carbon atoms of less than or equal to 150 grams per kilogram of reaction mixture.

The pentenoic acid is hydroxycarbonylated in the presence of a catalyst comprising rhodium and/or iridium and, optionally, other noble metals selected from ruthenium and osmium. The amount of catalyst to be employed can vary within wide limits.

In general an amount, expressed in moles of metallic iridium and/or metallic rhodium per liter of reaction mixture, of between $10^{-4}$ and $10^{-1}$ gives satisfactory results. Smaller amounts can be employed; however, it is observed that the rate of reaction is low. Larger amounts are disadvantageous only from an economic standpoint.

The concentration of iridium and/or rhodium is preferably between $5 \times 10^{-4}$ and $10^{-2}$ mol/liter.

By iodine- or bromine-containing promoter is meant, in the context of the process of the invention, HI and HBr and organic iodine compounds or organic bromine compounds which are capable of generating HI or HBr under the reaction conditions, and more particularly alkyl iodides and alkyl bromides having 1 to 10 carbon atoms. Methyl iodide and methyl bromide are recommended more particularly.

The promoter used is preferably an iodine-containing promoter and, more preferably, is HI or methyl iodide.

The amount of iodine- and/or bromine-containing promoter to be employed is generally such that the molar ratio of iodine (and/or bromine) to iridium (and/or rhodium) is greater than or equal to 0.1. It is generally preferable for this ratio to be less than or equal to 20. Preferably, the molar ratio of iodine (and/or bromine) to iridium (and/or rhodium) is between 1 and 5.

The presence of water is vital for conducting the hydroxycarbonylation. Generally speaking, the amount of water to be employed is such that the molar ratio of water to pentenoic acids is between 0.01 and 10.

A larger amount is undesirable owing to the loss in catalytic activity which is observed. At a given point in time the molar ratio of water to pentenoic acids in the reaction mixture may be less than the minimum value indicated above if the reaction is carried out, for example, with continuous injection of water rather than with the introduction of water together with the other charges before the hydroxycarbonylation reaction.

The molar ratio of water to pentenoic acids is preferably between 0.01 and 2, subject to the above comment regarding the minimum value.

The hydroxycarbonylation reaction can be carried out either in a separate solvent or in a large excess of pentenoic acids.

As a separate solvent it is possible in particular to use saturated aliphatic or aromatic carboxylic acids containing not more than 20 carbon atoms, provided that these acids are liquid under the reaction conditions. As examples of such carboxylic acids mention may be made of acetic, propionic, butyric, valeric, adipic, benzoic and phenylacetic acids.

The separate solvent can also be selected from saturated aliphatic or cycloaliphatic hydrocarbons and their chlorinated derivatives and aromatic hydrocarbons and their chlorinated derivatives, provided that these compounds are liquid under the reaction conditions. As examples of such solvents mention may be made of benzene, toluene, chlorobenzene, dichloromethane, hexane and cyclohexane.

When present in the reaction mixture the separate solvent makes up, for example, from 10 to 99% by volume relative to the total volume of the said reaction mixture and, preferably, from 30 to 90% by volume.

In a preferred variant the hydroxycarbonylation reaction is carried out in the pentenoic acids themselves, namely 2-pentenoic, 3-pentenoic and 4-pentenoic acids and mixtures thereof.

The hydroxycarbonylation reaction is conducted at a pressure which is greater than atmospheric pressure, and in the presence of carbon monoxide. It is possible to use substantially pure carbon monoxide or technical-grade carbon monoxide as is found in commerce.

The reaction is conducted in the liquid phase. The temperature is generally between 100 and 240° C. and preferably between 160 and 200° C.

The total pressure can vary within wide limits. The partial pressure of carbon monoxide, measured at 25° C., is generally from 0.5 to 50 bar and preferably from 1 to 25 bar.

As indicated above, the reaction mixture obtained from the hydroxycarbonylation reaction comprises essentially the unconverted pentenoic acids, water, the iodine- and/or bromine-containing promoter, the catalyst, the solvent (if employed), the resultant adipic acid, and the other byproducts, which are formed in greater or lesser quantities, such as, for example, 2-methylglutaric, 2-ethylsuccinic and valeric acids and gamma-valerolactone (or 4-methylbutyrolactone).

The at least partial separation of the branched diacids such that their concentration after recycling into the hydroxycarbonylation reactor does not exceed the upper limits indicated above, throughout the reaction, can be carried out by known methods. It is possible, for example, to convert all or some of the branched diacids into their corresponding anhydrides, as is described in the patent EP-A-0 687 663, in order to enable them to be separated more easily by distillation.

It is also possible to subject the reaction mixture which is obtained from the hydroxycarbonylation to fractional distillation and to remove the lightest compounds, such as the pentenoic acids or the other compounds having 5 carbon atoms. This first distillation can be carried out under atmospheric pressure directly or following separation of part of the resultant adipic acid by crystallization. Subsequently, the fractions richest in branch diacids can be distilled. This distillation can be supplemented by other operations for separating the various constituents of the reaction mixture obtained from the hydroxycarbonylation. In this way it is possible to carry out crystallization, and optionally one or more recrystallizations, of the adipic acid in order to recover as much as possible of the catalyst which it contains.

The branched diacids are distilled under reduced pressure, possibly and advantageously under a gentle stream of carbon monoxide.

It is possible in this way to recycle at least some of the catalyst, of the promoter and of the light compounds capable of being converted at least in part into adipic acid, while recycling only very little if any of the branched diacids.

Advantageously, the process of the invention is performed continuously. Indeed, apart from the obvious industrial advantage of this type of implementation, it is much easier to permanently maintain a relatively low level of branched diacids, the unavoidable formation of the said branched diacids and their partial recycling being compensated by the continuous withdrawal of a portion of the reaction mixture.

The concentration of branched diacids in the reaction mixture can then be maintained, for example, at a level of less than or equal to 100 grams per kilogram and, preferably, of less than or equal to 50 grams per kilogram.

Finally, among the branch diacids, it is found that it is even more advantageous for 2-ethylsuccinic acid to be maintained more specifically and within the reaction medium at a content of less than or equal to 50 grams per kilogram and, preferably, of less than or equal to 30 grams per kilogram. In the context of a continuous process, this content of 2-ethylsuccinic acid can then be maintained in the reaction medium at a level of less than or equal to 20 grams per kilogram and, preferably, of less than or equal to 10 kilograms per kilogram.

The examples which follow illustrate the invention.

EXAMPLES 1 TO 3

A 1 liter metal reactor equipped with means for heating and cooling, with a stirrer (operating at 1200 revolutions/minute), with devices for introducing the reactants and for withdrawal, and with devices for measuring the temperature and pressure is charged with:
2.52 mol of 3-pentenoic acid (P3)
0.924 mmol of IrCl(COD)
2.24 mmol of HI (57% by weight aqueous solution)

A pressure of 5 bar of CO is established at room temperature and then the reaction mixture is heated with stirring to 185° C., at which temperature the pressure is adjusted to 20 bar using CO. 22.7 g of water (1.26 mol) are then injected over 30 minutes.

After 30 minutes reaction, the reaction mixture is removed while still hot, under a carbon monoxide atmosphere, into a 500 ml pan.

A sample of this mixture is assayed by gas chromatography (GC) and high-performance liquid chromatography (HPLC).

The results are as follows:
degree of conversion (DC) of P3: 52%
yield (Y) of adipic acid (AdOH) relative to P3 converted: 68%
yield (Y) of branched diacids (2-methylglutaric and 2-ethylsuccinic acid) relative to P3 converted: 13%
yield (Y) of gamma-valerolactone (M4L) relative to P3 converted: 8%
rate of absorption of CO in moles per hour per liter of reaction mixture (approximately 280 ml): 5.8
linearity (L) (=ratio of adipic acid to total diacids obtained): 84%.

The mixture withdrawn is distilled using a column with a height of 250 cm, under atmospheric pressure, with CO being bubbled through.

This gives a fraction comprising unconverted pentenoic acid, gamma-valerolactone, valeric and methylbutanoic acids, and a portion of methylglutaric and ethylsuccinic acids.

Methylglutaric and ethylsuccinic acids are subsequently distilled under reduced pressure (with CO being bubbled through via a capillary tube).

The residue essentially contains adipic acid and the catalyst. The catalyst is recovered in the recrystallization and wash waters of the adipic acid.

After having replenished the catalyst and added the iodine-containing promoter and 3-pentenoic acid again, the hydroxycarbonylation of pentenoic acid is repeated as described above, with substantially the same amounts of reactants and under the same operating conditions, but with recycling of a portion of the branched diacids isolated beforehand.

The charges are as follows:
2.44 mol of 3-pentenoic acid (P3)
0.924 mmol of IrCl(COD)
2.24 mmol of HI (57% by weight aqueous solution)
11.5 g of branched diacids (41 g/kg of initial reaction mixture)
1.26 mol of water (22.7 g) injected over 30 minutes.

The reaction lasts for 30 minutes at 185° C., and quantitative determination gives the following results.
degree of conversion (DC) of P3: 53%
yield (Y) of adipic acid (AdOH) relative to P3 converted: 66%
yield (Y) of branched diacids (2-methylglutaric and 2-ethylsuccinic acid) relative to P3 converted: 15.5%
yield (Y) of gamma-valerolactone (M4L) relative to P3 converted: 8%
rate of absorption of CO in moles per hour per liter of reaction mixture (approximately 280 ml): 5.8
linearity (L) (=ratio of adipic acid to total diacids obtained): 81%
total content of branched diacids in the final reaction mixture: 134 g/kg.

The treatment described for Example 1 is carried out and, after the catalyst has been replenished and the iodine-containing promoter and 3-pentenoic acid have been added again the hydroxycarbonylation of pentenoic acid is repeated as described above, with substantially the same amounts of reactants and under the same operating conditions, but with recycling of a larger amount of the branched diacids isolated beforehand.

The charges are as follows:
2.35 mol of 3-pentenoic acid (P3)
0.924 mmol of IrCl(COD)
2.24 mmol of HI (57% by weight aqueous solution)
22.9 g of branched diacids (41.5 g/kg of initial reaction mixture)
1.26 mol of water (22.7 g) injected over 30 minutes.

The reaction lasts for 30 minutes at 185° C., and quantitative determination gives the following results.
degree of conversion (DC) of P3: 49%
yield (Y) of adipic acid (AdOH) relative to P3 converted: 65%
yield (Y) of branched diacids (2-methylglutaric and 2-ethylsuccinic acid) relative to P3 converted: 18.3%
yield (Y) of gamma-valerolactone (M4L) relative to P3 converted: 7%
rate of absorption of CO in moles per hour per liter of reaction mixture (approximately 280 ml): 5.2
linearity (L) (=ratio of adipic acid to total diacids obtained): 78%
total content of branched diacids in the final reaction mixture: 177 g/kg.

In the results obtained in Example 3, with a content of branched diacids of between 81.5 g/kg at the beginning of the hydroxycarbonylation and 177 g/kg at the end of the hydroxycarbonylation, it is observed that the rate of reaction and the linearity are beginning to decrease.

COMPARATIVE TEST 1

The recycling tests are repeated, with the introduction of larger amounts of methylglutaric and ethylsuccinic acids, the operating conditions being the same.

The charges are as follows:
2.21 mol of 3-pentenoic acid (P3)
0.924 mmol of IrCl(COD)
2.24 mmol of HI (57% by weight aqueous solution)
45.8 g of branched diacids (158 g/kg of initial reaction mixture)
1.26 mol of water (22.7 g) injected over 30 minutes.

The reaction lasts for 30 minutes at 185° C., and quantitative determination gives the following results.
degree of conversion (DC) of P3: 29%
yield (Y) of adipic acid (AdOH) relative to P3 converted: 53%
yield (Y) of branched diacids (2-methylglutaric and 2-ethylsuccinic acid) relative to P3 converted: 31.1%
yield (Y) of gamma-valerolactone (M4L) relative to P3 converted: 4%
rate of absorption of CO in moles per hour per liter of reaction mixture (approximately 280 ml): 2.8
linearity (L) (=ratio of adipic acid to total diacids obtained): 63%
total content of branched diacids in the final reaction mixture: 257 g/kg.

In the results obtained in Comparative Test 1, with a content of branched diacids of between 158 g/kg at the beginning of the hydroxycarbonylation and 257 g/kg at the end of the hydroxycarbonylation, it is observed that the rate of reaction and the linearity of the diacids obtained decrease very greatly.

What is claimed is:

1. A process for hydroxycarbonylating pentenoic acid by reaction with water and carbon monoxide in the presence of a catalyst comprising at least rhodium and/or iridium and of an iodine-containing and/or bromine-containing promoter, comprising recycling in the reaction mixture at least part of the unreacted pentenoic acid, the catalyst and the promoter contained in the final reaction mixture, wherein, before recycling the unreacted pentenoic acid, the catalyst and the promoter, at least a part of the branched carboxylic diacids having 6 carbons produced by the hydroxycarbonylation reaction is separated and not recycled together with the unreacted pentenoic acid, catalyst and promoter in order to maintain the amount of said branched carboxylic diacids at a level less than or equal to 200 grams per kilogram of reaction mixture.

2. The process according to claim 1, wherein the hydroxycarbonylation reaction is conducted in the presence of an amount of branched carboxylic diacids having 6 carbon atoms of less than or equal to 150 grams per kilogram of reaction mixture.

3. The process according to claim 1, wherein the hydroxycarbonylation reaction is carried out in the presence of a catalyst comprising rhodium and/or iridium or, optionally, other noble metals selected from ruthenium and osmium.

4. The process according to claim 1, wherein the concentration of catalyst employed, expressed as moles of metallic iridium and/or metallic rhodium per liter of reaction mixture, is between $10^{-4}$ and $10^{-1}$ mole/liter.

5. The process according to claim 1, wherein the iodine- and/or bromine-containing promoter comprises HI, HBr, organic iodine compounds or organic bromine compounds which are capable of generating HI or HBr under the reaction conditions.

6. The process according to claim 1, wherein the promoter used is an iodine-containing promoter.

7. The process according to claim 1, wherein the molar ratio of iodine and/or bromine promoter to iridium and/or rhodium catalyst is greater than or equal to 0.1.

8. The process according to claim 1, wherein the molar ratio of water to pentenoic acids is between 0.01 and 10.

9. The process according to claim 1, wherein the hydroxycarbonylation reaction is conducted either in a separate solvent or in a large excess of pentenoic acids.

10. The process according to claim 9, wherein the separate solvent comprises saturated aliphatic or aromatic carboxylic acids containing not more than 20 carbon atoms, saturated aliphatic or cycloaliphatic hydrocarbons and their chlorinated derivatives, or aromatic hydrocarbons and their chlorinated derivatives, provided that these compounds are liquid under the reaction conditions.

11. The process according to claim 1, which is performed continuously, and wherein the concentration of branched diacids in the reaction mixture is less than or equal to 100 grams per kilogram of reaction mixture.

12. The process according to claim 4, wherein the concentration of catalyst employed is between $5\times10^{-4}$ and $10^{-2}$ mole/liter.

13. The process according to claim 5, wherein the iodine- and/or bromine-containing promoter comprises alkyl iodides and/or alkyl bromides having 1 to 10 carbon atoms.

14. The process according to claim 6, wherein the promoter comprises HI or methyl iodide.

15. The process according to claim 7, wherein the molar ratio of iodine and/or bromine promoter to iridium and/or rhodium catalyst is less than or equal to 20.

16. The process according to claim 11, wherein the concentration of branched diacids in the reaction mixture is less than or equal to 50 grams per kilogram of reaction mixture.

* * * * *